United States Patent [19]

Haddad et al.

[11] Patent Number: 5,093,298

[45] Date of Patent: * Mar. 3, 1992

[54] MALEIC ANHYDRIDE CATALYSTS

[75] Inventors: Muin S. Haddad; William S. Eryman, both of Naperville, Ill.

[73] Assignee: Amoco Corporation, Chicago, Ill.

[ * ] Notice: The portion of the term of this patent subsequent to Sep. 18, 2007 has been disclaimed.

[21] Appl. No.: 560,386

[22] Filed: Jul. 31, 1990

Related U.S. Application Data

[63] Continuation of Ser. No. 387,001, Jul. 28, 1989, Pat. No. 4,957,894, which is a continuation-in-part of Ser. No. 225,523, Jul. 28, 1988, abandoned.

[51] Int. Cl.$^5$ .................... B01J 27/198; B01J 37/28
[52] U.S. Cl. .................... 502/209; 502/210; 502/211
[58] Field of Search ................ 502/209-213

[56] References Cited

U.S. PATENT DOCUMENTS

| | | | |
|---|---|---|---|
| 4,418,003 | 11/1983 | Udovich et al. | 502/209 |
| 4,515,904 | 5/1985 | Edwards | 502/209 |
| 4,567,158 | 1/1986 | Wrobleski et al. | 502/209 |
| 4,652,543 | 3/1987 | Edwards et al. | 502/209 |
| 4,699,895 | 10/1987 | Edwards | 502/209 |
| 4,701,433 | 10/1987 | Edwards | 502/209 |
| 4,732,885 | 3/1988 | Edwards et al. | 502/209 |
| 4,933,312 | 6/1990 | Haddad et al. | 502/209 |
| 4,957,894 | 9/1990 | Haddad et al. | 502/209 |

Primary Examiner—Paul E. Konopka
Attorney, Agent, or Firm—Margaret M. Duncan; William H. Magidson; Ralph C. Medhurst

[57] ABSTRACT

Novel maleic anhydride catalysts comprising phosphorus-vanadium oxides and phosphorus-vanadium-co-metal oxides and the process for making such catalysts are disclosed. These catalysts under reaction conditions for the manufacture of maleic anhydride from butane feedstock do not expand to the point of crushing and producing fines. Moreover, the halogen level of such a catalyst is reduced.

4 Claims, No Drawings

MALEIC ANHYDRIDE CATALYSTS

CROSS-REFERENCE TO RELATED APPLICATION

This application is a continuation application of copending application U.S. Ser. No. 387,001, filed in the U.S. Patent and Trademark Office on July 28, 1989, now U.S. Pat. No. 4,957,894, issued on Sept. 18, 1990, which is a continuation-in-part application of U.S. Ser. No. 225,523, filed in the U.S. Patent and Trademark Office on July 28, 1988, and now abandoned.

FIELD OF THE INVENTION

The field of this invention relates to novel catalysts and to processes for the manufacture of phosphorus-vanadium mixed oxide and phosphorus-vanadium-co-metal mixed oxide catalysts suitable for the oxidation of benzene, butane, butene, and butadiene to maleic anhydride wherein under oxidation conditions of the hydrocarbon the catalyst particles do not expand and the level of chlorine in the catalyst is reduced.

BACKGROUND

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs.

In general, catalysts proposed for the oxidation of butane to maleic anhydride have been based upon vanadium and phosphorus. In U.S. Pat. No. 3,293,268, it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 weight percent are reported. Various activators, stabilizers, and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; 4,403,943; 4,154,703; and British Application 2,019,839A. While the aforementioned prior art tends to bring about some improvement in the performance of the phosphorus-vanadium catalyst, there remains much room for improvement, particularly from the standpoint of high conversion, yield, and catalyst life. Other references of interest include U.S. Pat. Nos. 4,020,174; 4,094,816; 4,089,807; 3,296,282; 3,474,041; and British Patent 1,464,198. All of these references relate to catalyst regeneration and not to catalyst stability.

Also, U.S. Pat. Nos. 3,915,892 and 3,985,775 teach a process for preparing catalysts suitable for preparing maleic anhydride from n-butane comprising a mixed vanadium-phosphorus oxide wherein one of the process steps consists of heating the components to between 350° C. (662° F.) and 410° C. (770° F.) in an oxygen-containing gas. The function of this step is to remove water of hydration from the dihydrate of the mixed oxide of the vanadium and pentavalent phosphorus complex. These patents do not teach the use of air or other oxygen-containing gas in the catalyst reaction step or in the drying step for removing the bulk of the water or other reaction solvents.

SUMMARY OF THE INVENTION

According to the present invention, there is provided a catalyst for the production of maleic anhydride by the oxidation of butane, which catalyst comprises a phosphorus-vanadium mixed oxide and a small amount of halogen, the atomic ratio of vanadium to phosphorus being in the range of about 0.5:1 to about 1.25:1, said catalyst being prepared in a reaction zone containing a first atmosphere comprising at least about 0.1 weight percent oxygen and subsequently in a drying zone containing a second atmosphere comprising at least about 0.1 weight percent oxygen, said first atmosphere being maintained by introducing an oxygen-containing gas into said reaction zone in an amount and at a rate that are sufficient to provide said first atmosphere, and said second atmosphere being maintained by introducing an oxygen-containing gas into said drying zone in an amount and at a rate that are sufficient to provide said second atmosphere, said catalyst having the ability not to expand when employed at a temperature of about 343° C. (650° F.) to about 510° C. (950° F.) in the production of maleic anhydride from butane.

In addition, there is provided a process for the manufacture of the catalyst.

DESCRIPTION AND PREFERRED EMBODIMENTS

An improved catalyst for the production of maleic anhydride by the oxidation of butane or other $C_4$ hydrocarbons has been developed. This catalyst has the ability not to expand appreciably when employed at a temperature in the range of about 343° C. (650° F.) to about 510° C. (950° F.) in the production of maleic anhydride from butane. As used herein, the term "not to expand appreciably" means that expansion of the catalyst does not exceed two percent.

According to the present invention, there is provided a catalyst for the production of maleic anhydride by the oxidation of butane or other $C_4$ hydrocarbons, which catalyst comprises a phosphorus-vanadium mixed oxide and a small amount of halogen, the atomic ratio of vanadium to phosphorus being in the range of about 0.5:1 to about 1.25:1, said catalyst being prepared in a reaction zone containing a first atmosphere comprising at least about 0.1 weight percent oxygen and subsequently in a drying zone containing a second atmosphere comprising at least about 0.1 weight percent oxygen, said first atmosphere being maintained by introducing an oxygen-containing gas into said reaction zone in an amount and at a rate that are sufficient to provide said first atmosphere and said second atmosphere being maintained by introducing an oxygen-containing gas into said drying zone in an amount and at a rate that are sufficient to provide said second atmosphere, said catalyst having the ability not to expand appreciably when employed at a temperature of about 343° C. (650° F.) to about 510° C. (950° F.) in the production of maleic anhydride from butane.

While typically the reaction zone and the drying zone are separate zones, it is conceivable that they could be one and the same zone.

Our catalyst is suitably prepared in organic solvents by slurrying vanadium compounds and metals or metal oxides such as molybdenum oxide, zinc oxide, uranium oxide, tungsten oxide, tin oxide, bismuth oxide, titanium oxide, niobium oxide, antimony oxide, and cobalt oxide in organic solvents, preferably organic ether solvents.

A small amount of water or a hydrogen donor compound, such as a lower alcohol, is also present in the ether. Suitable alcohols are ethanol and methanol and suitable ethers are tetrahydrofuran (THF), tetrahydropyran, 1,2-dimethoxyethane, bis(2-methoxyethyl)ether, 1,4-dioxane, ethylether, propylether, butylether, and pentylether. Phosphoryl halide is slowly added to the slurry. The water or hydrogen donor reacts with the phosphoryl halide to generate anhydrous phosphoric acid or phosphate esters and hydrogen halide gas. The hydrogen halide dissolves both the vanadium compound, for example, the vanadium pentoxide, and the co-metal compound and also reduces the vanadium from a valence state of about five to a valence state of about four. This reaction takes places at a temperature of about 0° C. (32° F.) to about 200° C. (392° F.).

While the reaction solution is being refluxed, if desired, a modifier or mixture of modifiers such as o-xylene, m-xylene, p-xylene, benzene, toluene, mesitylene, pseudocumene, phthalic anhydride, trimellitic anhydride, benzoic acid, toluic acid, phthalic acid, isophthalic acid, terephthalic acid, trimesic acid or trimellitic acid, is suitably added to the reaction solvent. After refluxing, the color of the solution is green. The volume of the solution is reduced by distillation or evaporation until it becomes a thick syrup. This syrup is dried at a temperature of about 130° C. (266° F.) to about 200° C. (392° F.) and 0–15 inches of mercury vacuum. Once dry, the color of the solid material is brown. The catalyst can be formed into geometric forms, such as cylinders, using graphite, Sterotex or other lubricants such as stearic acid, zinc stearate or starch and binders such as polyvinyl alcohol. The catalyst in the form of geometric shapes or in powder form is suitably calcined in air or a nitrogen-air combination before loading into a suitable tubular reactor. The catalyst is activated further by the addition of water and phosphorus compounds or mixtures thereof such as alkylphosphates, phosphites, and phosphines. This activation takes place at a temperature of about 300° C. (572° F.) to about 500° C. (932° F.). Representative phosphorus compounds have the following structures:

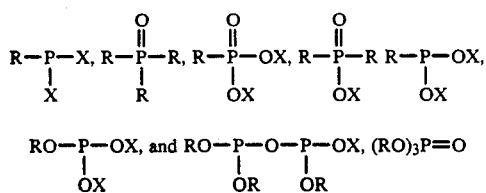

wherein R is phenyl or an alkyl radical of 1 to 6 carbon atoms and X is H or R. Suitable compounds are primary, $RPH_2$, secondary, $R_2PH$, and tertiary, $R_3P$, phosphines, such as ethyl phosphine; the tertiary phosphine oxides, $R_3PO$, such as tripropyl phosphine oxide, the primary, $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the phosphinous acids $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1$–$C_4$ alkyl, at least one R being a $C_1$–$C_4$ alkyl The preferred phosphorus compounds are triethylphosphate and trimethylphosphate.

Our novel catalyst for the production of maleic anhydride comprising a phosphorus-vanadium mixed oxide or a phosphorus-vanadium-co-metal mixed oxide is prepared in an atmosphere comprising at least about 0.1 weight percent oxygen of the total gas blanketing the reaction. In fact, the catalyst is prepared by reacting and refluxing the reaction mixture in an atmosphere comprising at least about 0.1 weight percent oxygen and by drying the reaction product in an atmosphere comprising at least about 0.1 weight percent oxygen. A suitable atmosphere comprises about 0.1 weight percent to about 50 weight percent oxygen. Typically, the atmosphere comprises about 0.1 weight percent to about 21 weight percent oxygen. However, when using an atmosphere in excess of 10 weight percent to about 11 weight percent oxygen, extreme caution must be used. Oxygen levels above these latter two values are in the flammability range. For safety considerations, a range of about 0.1 weight percent to about 11 weight percent oxygen is preferred. A range of about 3 weight percent to about 9 weight percent oxygen is more preferred for any of the atmospheres used in the reaction zone or the drying zone when preparing the catalyst of the present invention.

The usual gas blanketing the reaction is nitrogen but helium and other inert gases can be utilized. It should be noted that if the catalyst is prepared in a totally inert atmosphere without oxygen being present, catalysts are formed which will expand and in some instances may expand to the point of being crushed in a tubular reactor. These catalysts cannot be used in commercial operations requiring fixed bed reactors wherein the catalysts are charged into steel tubes because the pressure drop across the catalyst bed will be excessive. Catalysts prepared in an inert atmosphere also have a high chlorine content. This halogen is detrimental to oxidation equipment. Our novel catalysts have much less halogen and, therefore, are more useful in that respect. The data for the lower chlorine content are shown in Table I.

The novel catalyst comprises a phosphorus-vanadium mixed oxide or a phosphorus-vanadium mixed oxide promoted by metals. The atomic ratio of the vanadium to phosphorus can suitably be in the range of 0.5:1 to 1.25:1.0. The total atomic ratio of vanadium to phosphorus advantageously is in the range of 0.75:1 to 1:1. It is preferred that the total atomic ratio of molybdenum, zinc, tungsten, uranium, tin, bismuth, titanium, niobium or cobalt to vanadium should be in the range of 0.001:1 to 0.2:1.

The co-metal, such as molybdenum, zinc, tungsten, uranium, bismuth, titanium, antimony, niobium, cobalt or tin may be added as a compound together with vanadium, or separately introduced into the solution. Suitable co-metal compounds comprise their oxides and soluble salts. Suitable molybdenum compounds comprise molybdenum oxide and most soluble molybdenum salts. If it is desired to improve physical properties of the catalysts, they may be treated with the suspension of an inert support, for example, alumina, titania, silicon carbide, kieselguhr, pumice, or silica. The catalyst may be reinforced with such materials at any stage in its preparation.

According to our process, the average valence of vanadium is in the range of about 3.8 to 4.2.

In our catalyst preparation, various phosphoryl halides may be used, but POCl$_3$ is preferred. Hence, some halogen will remain in the catalyst. The halogen will be present as a substituent in an organic molecule and/or as a negative halogen ion, such as a halide ion.

The catalyst can be activated in the presence of the reaction feed gas stream, water, and a suitable phosphorus-containing compound selected from the following compounds:

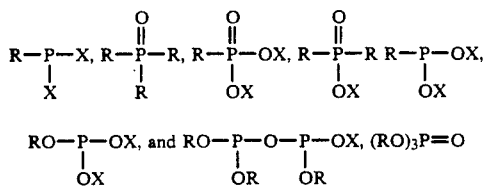

wherein R is phenyl or an alkyl radical of 1 to 6 carbon atoms and X is H or R. Suitable compounds are the primary, RPH$_2$, secondary, R$_2$PH, and tertiary, R$_3$P, phosphines, such as ethyl phosphine; the tertiary phosphine oxides, R$_3$PO, such as tripropyl phosphine oxide; the primary, RP(O)(OX)$_2$, and secondary, R$_2$P(O)OX, phosphonic acids, such as benzene phosphonic acid; the esters of the phosphonic acids, such as diethyl methanephosphonate; the phosphonous acids, RPO$_2$X$_2$, such as benzenephosphonous acid and the esters thereof such as the monoethyl ester; the phosphinous acids, R$_2$POX, such as diethyl phosphinous acid and the esters thereof, such as the monoethyl ester; the primary, ROP(OX)$_2$, secondary, (RO)$_2$POX, and tertiary, (RO)$_3$P, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula (RO)$_3$P=O wherein R is hydrogen or a C$_1$-C$_4$ alkyl, at least one R being a C$_1$-C$_4$ alkyl. The preferred phosphate compounds are triethylphosphate and trimethylphosphate.

The amount of water added is about 1,000 to about 40,000 parts per million of the reaction feed gas stream. The reaction feed gas stream comprises normal-butane and/or another C$_4$-hydrocarbon and air. Other C$_4$-hyrocarbons are butene, isobutane, isobutene, and butadiene.

Suitable vanadium compounds include: vanadium oxides, such as vanadium pentoxide, vanadium trioxide, and the like; vanadium oxyhalides, such as vanadyl chloride, vanadyl dichloride, vanadyl trichloride, vanadyl bromide, vanadyl dibromide, vanadyl tribromide and the like; vanadium-containing acids, such as metavanadic acid, pyrovanadic acid, and the like; vanadium salts, such as ammonium meta-vanadate, vanadium sulfate, vanadium phosphate, vanadyl formate, vanadyl oxalate, and the like; however, vanadium pentoxide is preferred.

As pointed out hereinabove, there is provided a process for the manufacture of a catalyst that is suitable for use in the manufacture of maleic anhydride from butane, said catalyst comprising a phosphorus-vanadium mixed oxide and a small amount of a halogen. This process comprises reacting in a reaction zone at a temperature of about 0° C. (32° F.) to about 200° C. (392° F.) a vanadium compound in an organic ether solvent having about 2 to about 10 carbon atoms with a phosphoryl halide in the presence of water or an aliphatic alcohol having from about 1 to about 8 carbon atoms, said reacting being carried out by adding said phosphoryl halide to said vanadium compound in said organic ether solvent and forming a reaction mixture, refluxing said reaction mixture, introducing an oxygen-containing gas into said reaction zone and said reaction mixture during said reacting and said refluxing in an amount and at a rate that are sufficient to provide a first atmosphere comprising at least about 0.1 weight percent oxygen, forming a thick syrup, and drying said syrup in a drying zone in a second oxygen-containing atmosphere to form a solid catalytic material, said second atmosphere being maintained by introducing into said drying zone an oxygen-containing gas in an amount and at a rate that are sufficient to provide an atmosphere comprising at least about 0.1 weight percent oxygen. Optionally, at least a portion of the solvent may be eliminated prior to drying. A combination of several variables, such as oxygen concentration in the gas being employed, amount of gas used, and rate of gas used, will determine the weight percent oxygen in the atmosphere being maintained.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic mixtures of oxygen and diluent gases, such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4,000 cc of feed per cc of catalyst per hour, and more preferably about 1,000 to 2,400 cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 20° C. (32° F.). A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature-regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone under an inert material such as one-quarter-inch Alundum pellets, inert ceramic balls, nickel balls, or chips, and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 11°-28° C. (20°-50° F.) above the salt bath temperature. The temperature of the reactor, of course, will also depend to some extent upon the size of the reactor and the butane concentration.

The reaction may be conducted at atmospheric, superatmospheric, or subatmospheric pressure. The exit pressure will be at least slightly higher than the ambient pressure to ensure a positive flow from the reactor. The pressure of the inert gases must be sufficiently high to overcome the pressure drop through the reactor.

Maleic anhydride may be recovered by a number of ways well-known to those skilled in the art. For example, the recovery may be by direct condensation or by absorption in suitable media, with specific operations and purification of the maleic anhydride. The following examples will serve to provide full understanding of the invention, but it is to be understood that these examples are given for illustrative purposes only and will not be interpreted as limiting the invention in any way.

Maleic anhydride is currently produced by fixed bed catalytic oxidation of butane over mixed vanadium oxide catalyst. The catalyst is usually formed into tablets prior to loading in the multitubular reactor. The size and shape of these tablets are important since they determine the void fraction available in the reactor. It is important that this void fraction be large enough to avoid development of a large pressure drop across the reactor. One such suitable tablet is a right cylinder. In addition to its dependence on the shape and dimensions of the tablet, the reactor's void fraction depends on whether those dimensions change under hydrocarbon conversion conditions. For example if the tablet undergoes a volume increase or "expansion" the void fraction will decrease and an unacceptable increase in pressure drop will result. We discovered that tablets made from calcined catalyst powder underwent an unexpected expansion in a standard expansion test as well as under hydrocarbon conversion conditions in a large pilot plant. This expansion resulted in unacceptably high pressure drop across the catalyst bed. We discovered that tablet expansion is caused by the absence of oxygen from the atmosphere during the synthesis of the catalyst. We also discovered that oxygen absence from the reaction and the drying step resulted in higher than desired chlorine concentration in the catalyst. Lower chlorine content is desirable since it reduces the probability of equipment corrosion when the catalyst powder is calcined and when the catalyst is operated in a commercial plant.

TYPICAL CATALYST PREPARATION

To a 3-liter, 3-neck, round bottom flask equipped with a thermowell, electrical mantle, mechanical stirrer, and reflux condenser, were added 364 g $V_2O_5$, 17.28 g $MoO_3$, 270 g water, and 1,000 ml tetrahydrofuran (THF). $POCl_3$ (767 g) was added from an addition funnel over a period of 2 hours. During the $POCl_3$ addition an exothermic reaction occurs which results in a continuous temperature rise, reflux of the solvent and dissolution of the solids. The mixture turns from a yellow orange slurry to red brown solution as the $POCl_3$ addition progresses. At the end of $POCl_3$ addition, the deep green solution is heated up to reflux and maintained at reflux for two hours. As an optional step the deep green solution is then partially (500 ml) stripped of solvent. The thick black, green syrup is then dried overnight at about 3 in. of Hg vacuum with a mild air, nitrogen, or $N_2$/air purge passing through the oven. Drying temperature and time vary from 130° C. (266° F.) to 200° C. (392° F.) and 18 to 48 hours respectively.

The dark brown catalyst powder is ground, calcined at 300° C. (572° F.) in air for 4 hours and formed into 3/16" cylindrical tablets using 5 wt % graphite as a lubricant. The side crush strength of the tablets is about 5.9 lbs.

EXPANSION TEST

In an expansion test the length and diameter of 10 tablets are measured with a caliper. An average volume is determined using the volume relationship for a cylinder. The tablets are then introduced to an oven at 482° C. (900° F.). The tablets are kept at that temperature in a humid air stream for 2 hours. The tablets are removed from the oven and allowed to cool in a desiccator. The length and diameter of the tablets are measured and an average volume is determined. The comparison of the average volume of the tablet before and after introduction to the oven determines whether the tablets expanded, shrank, or remained the same.

EFFECT OF ATMOSPHERE ON TABLET EXPANSION

The following examples demonstrate introducing oxygen (from air) during the reaction step of the catalyst synthesis results in powder whose tablets do not expand as much as those conducted in oxygen limited atmosphere.

EXAMPLE I

A catalyst synthesis was conducted as described above except that the reaction was blanketed with $N_2$, refluxed for 6 hours and was not stripped. The syrup was dried in $N_2$/air. Catalyst tablets showed an expansion of 5.7%.

EXAMPLE II

A synthesis was carried out as described for Example I except for air in the head space of the glassware. Air was not intentionally introduced. Catalyst tablets showed a shrinkage of +0.85%.

EXAMPLE III

This Example is similar to Example II except a 2 hour reflux was carried out. Catalyst tablets showed an equivalent shrinkage of +0.63%.

EXAMPLE IV

In this Example the reaction was run according to Example III except an air blanket was used during the POCl$_3$ addition and an intermittent air flow was used during the two hour reflux periods. Catalyst tablets showed the largest shrinkage of +4%.

EXAMPLE V

In this Example the reaction was carried out in a similar fashion to Example IV except air was bubbled in the liquid during the POCl$_3$ addition and reflux period.

Examples I-V clearly demonstrate that the use of air as the reaction atmosphere has a beneficial effect as compared with the use of N$_2$. The largest tablet expansion we observed was when the reaction was carried out under a nitrogen atmosphere, while the largest shrinkage was observed when air was introduced during the reaction.

EFFECT OF REACTION AND DRYING ATMOSPHERE ON CHLORIDE CONTENT OF THE CATALYST

In order to demonstrate the effect of reaction and drying atmosphere on the chloride content in the catalyst we carried out two preparations that were four times the scale described in Examples I-V. In one, a nitrogen blanket was used and, in the other, air was provided from the head space of the equipment. The solvent was partially stripped after the two hour reflux period and further refluxed for another 16 hours. Syrup samples were dried under four sets of drying conditions. The chlorine content of the catalyst and the drying conditions are shown in Table I.

The data in Table I demonstrates that the reaction atmosphere in both the reaction and drying steps affects the resulting chlorine content of the catalyst. The lowest chlorine concentration was observed for a catalyst whose synthesis was carried out in air and dried in air.

TABLE I

| Chloride Content of the Maleic Anhydride Catalyst | | | |
|---|---|---|---|
| Reaction Atmosphere | Drying Atmosphere | Drying Rate$^a$ | Cl, wt. % |
| N$_2$ | N$_2$ | Slow | 3.72 |
| N$_2$ | Air | Slow | 2.7 |
| N$_2$ | N$_2$ | Fast | 3.31 |
| N$_2$ | Air | Fast | 2.5 |
| N$_2$ | N$_2$ | Moderate | 3.53 |
| Air | N$_2$ | Slow | 2.33 |
| Air | Air | Slow | 1.96 |
| Air | N$_2$ | Fast | 3.52 |
| Air | Air | Fast | 1.87 |
| Air | N$_2$ | Moderate | 2.63 |

$^a$Slow drying was carried out at 130° C. (266° F.) for 26 hours followed by 18 hours at 180° C. (356° F.). Fast drying was carried out at 180° C. (356° F.) for about 18 hours. Moderate drying was carried out at 137° C. (279° F.) for 18 hours, 160° C. (320° F.) for 24 hours and 180° C. (356° F.) for 6 hours.

In general, the use of our novel process reduced the chlorine content of the catalyst from about 4 wt. % t about 1.8 to 2 wt. %. This is a very significant improvement since chlorine in the catalyst tends to deteriorate the reaction vessels.

EXAMPLES VI-XI

The effect of reaction and drying atmospheres on our catalyst tablet expansion was further demonstrated in a series of six preparations. These preparations are referred to here as Examples VI-XI.

For all Examples, typically the reactor contents (expressed as parts by weight) were comprised of 15 parts V$_2$O$_5$, 0.7 parts MoO$_3$, 11 parts H$_2$O, 41 parts tetrahydrofuran (THF) and 32 parts POCl$_3$. For the reaction step, the POCl$_3$ addition time was 2-4 hours and reflux time was about 2-5 hours. For the drying step, the temperature was in the range of 130° C. (266° F.) to 200° C. (392° F.), and the drying time was in the range of 20-50 hours. A purge gas of either pure N$_2$ or 91 wt % N$_2$/9 wt % O$_2$ was used at a rate of 0.1-1.0 standard cubic feet per hour per pound of V$_2$O$_5$. For each preparation, the dry powder was ground, calcined at 300° C. (572° F.) for four hours, and formed into 3/16" cylindrical tablets using 5 wt % graphite as a lubricant. The volume change of the tablets was then determined in our typical expansion test.

The composition of the purge gas and tablet volume change are shown in Table II. The data show clearly that the use of oxygen in Examples IX-XI results in powder whose tablets undergo volume shrinkage as compared with volume expansion in Examples IV-VIII where no oxygen was used.

TABLE II

| Effect of Purge Gas Composition on Maleic Anhydride Catalyst Tablet Volume Change | | |
|---|---|---|
| Example | Reaction and Drying Purge Gas | Tablet Volume Change |
| VI | N$_2$ | +26% |
| VII | N$_2$ | +11% |
| VIII | N$_2$ | +13% |
| IX | N$_2$/O$_2$ | −4.6% |
| X | N$_2$/O$_2$ | −6.5% |
| XI | N$_2$/O$_2$ | −4.4% |

What is claimed is:

1. A catalyst for the production of maleic anhydride by the oxidation of butane, benzene, butene or butadiene, the catalyst comprising a phosphorus-vanadium mixed oxide and a halogen, the atomic ratio by vanadium to phosphorus being in the range of about 0.5:1 to about 1.25:1, said catalyst being prepared in a reaction zone at a temperature of between about 0° C. (32° F.) to about 200° C. (392° F.) by the steps of:

(a) reacting a vanadium compound in an organic ether solvent having from about 2 to about 10 carbon atoms with a phosphoryl halide in the presence of water or an aliphatic alcohol having from about 1 to about 8 carbon atoms;

(b) refluxing said reaction mixture and forming a thick a syrup; and (c) drying said syrup to form a solid catalytic material, wherein said reacting, refluxing and drying steps are carried out in an atmosphere comprising at least about 0.1 wt. % oxygen, by introducing an oxygen-containing gas into said reacting, refluxing and drying steps in an amount and at a rate sufficient to provide said atmosphere, and wherein said catalyst has a halogen content from about 1.8 to about 2 wt. % of total catalyst weight and possesses a maximum expansion of about 2% or a maximum contraction of about 10% when used in the production of maleic anhydride at a temperature of about 343° C. (650° F.) to about 510° C. (950° F.)

2. The catalyst of claim 1, wherein said catalyst comprises a co-metal as a promoter, the ratio of said co-metal to said vanadium being in the range of about 0.001:1 to about 0.4:1.

3. The catalyst of claim 1, wherein said halogen is chlorine.

4. The catalyst of claim 2, wherein said co-metal is selected from the group consisting of molybdenum, zinc, tungsten, uranium, tin, bismuth, titanium, antimony, niobium, and cobalt.

* * * * *

UNITED STATES PATENT AND TRADEMARK OFFICE
CERTIFICATE OF CORRECTION

PATENT NO. : 5,093,298

DATED : March 3, 1992

INVENTOR(S) : Muin S. Haddad and William S. Eryman

It is certified that error appears in the above-identified patent and that said Letters Patent is hereby corrected as shown below:

| Column | Line(s) | |
|--------|---------|---|
| 4 | 5 | printed text reading "alkyl The preferred" should read --alkyl. The preferred--; |
| 6 | 57 | printed text reading "at 20°C. (32°F)" should read --at 0°C (32°F)--; |
| 9 | 67 | printed text reading "4 wt.% t" should read --4 wt.% to--; and |
| 10 | 48 | printed text reading "the atomic ratio by vanadium" should read --the atomic ratio of vanadium--. |

Signed and Sealed this

Third Day of August, 1993

Attest:

MICHAEL K. KIRK

*Attesting Officer*      *Acting Commissioner of Patents and Trademarks*